(12) United States Patent
Montegrande

(10) Patent No.: US 7,074,189 B1
(45) Date of Patent: Jul. 11, 2006

(54) ENDOSCOPICALLY DELIVERABLE ULTRASOUND IMAGING SYSTEM AND METHOD OF USE

(76) Inventor: Valentino Montegrande, 1150 Main St., Irvine, CA (US) 92614

( * ) Notice: Subject to any disclaimer, the term of this patent is extended or adjusted under 35 U.S.C. 154(b) by 0 days.

(21) Appl. No.: 10/720,999

(22) Filed: Nov. 24, 2003

Related U.S. Application Data

(63) Continuation-in-part of application No. 10/120,721, filed on Apr. 11, 2002, now Pat. No. 6,654,629.

(60) Provisional application No. 60/428,442, filed on Nov. 22, 2002, provisional application No. 60/351,122, filed on Jan. 23, 2002.

(51) Int. Cl.
*A61B 8/12* (2006.01)

(52) U.S. Cl. .................................................... 600/462

(58) Field of Classification Search ................ 600/443, 600/447, 437, 459–471, 101, 103; 128/899
See application file for complete search history.

(56) References Cited

U.S. PATENT DOCUMENTS

| | | | | |
|---|---|---|---|---|
| 3,927,661 A | * | 12/1975 | Takemura .................. | 600/445 |
| 4,582,067 A | * | 4/1986 | Silverstein et al. ......... | 600/455 |
| 4,802,487 A | * | 2/1989 | Martin et al. ............... | 600/463 |
| 5,178,150 A | * | 1/1993 | Silverstein et al. ......... | 600/463 |
| 5,255,681 A | * | 10/1993 | Ishimura et al. ............ | 600/437 |
| 5,351,693 A | * | 10/1994 | Taimisto et al. ............ | 600/465 |
| 5,803,083 A | * | 9/1998 | Buck et al. ................. | 600/439 |
| 5,878,749 A | * | 3/1999 | Miller ........................ | 128/898 |
| 5,957,846 A | * | 9/1999 | Chiang et al. .............. | 600/447 |
| 6,654,629 B1 | * | 11/2003 | Montegrande ............. | 600/424 |

* cited by examiner

*Primary Examiner*—Francis J. Jaworski
(74) *Attorney, Agent, or Firm*—Eric Karich

(57) ABSTRACT

An ultrasound imaging system has an ultrasound probe adapted to be placed in an instrument working channel of an endoscope, the ultrasound probe having a probe housing; an ultrasound transducer mounted within the probe housing; and an elongate flexible cord extending from the probe housing, the elongate flexible cord being adapted to fit through the instrument working channel of the endoscope and operably connect the ultrasound transducer with a computer.

4 Claims, 11 Drawing Sheets

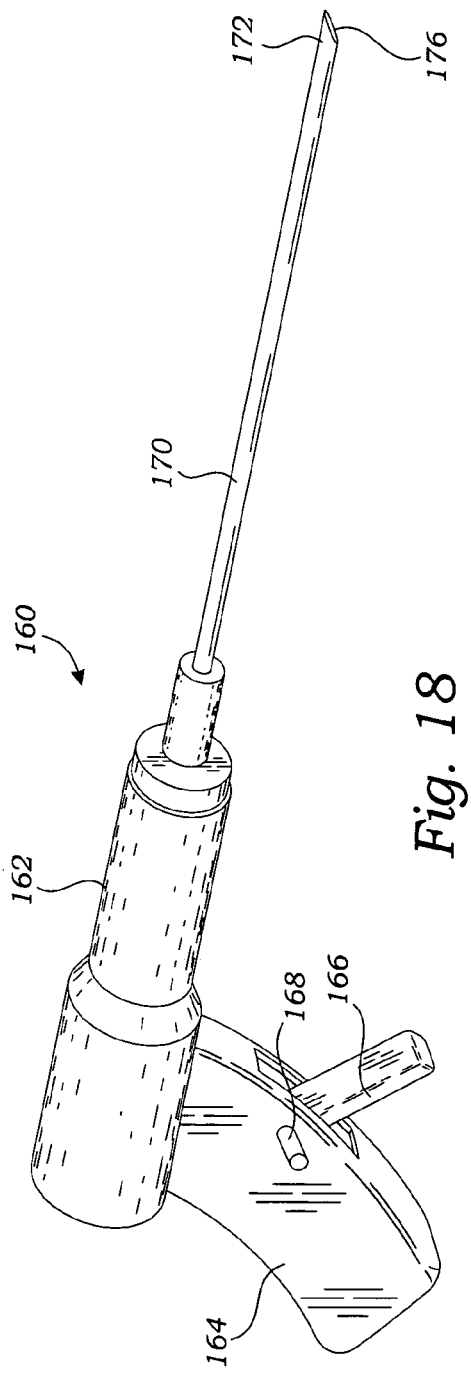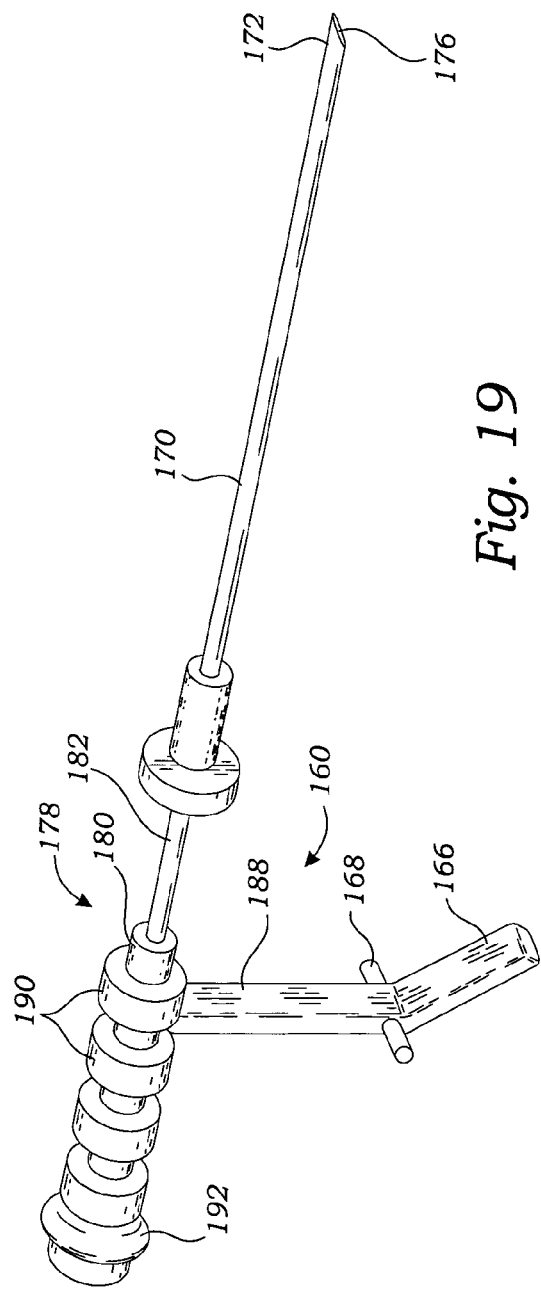

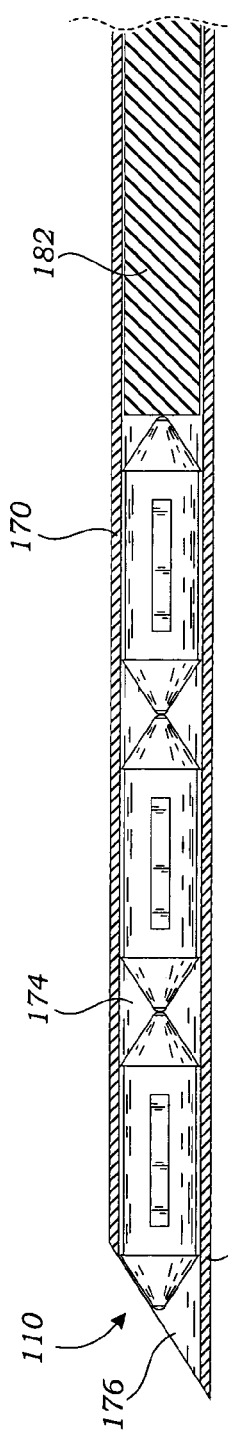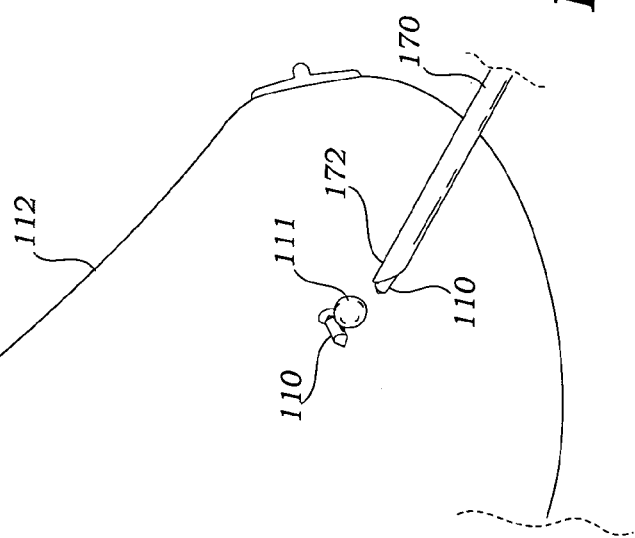

ENDOSCOPICALLY DELIVERABLE ULTRASOUND IMAGING SYSTEM AND METHOD OF USE

CROSS-REFERENCE TO RELATED APPLICATIONS

This application for a Utility patent is a continuation-in-part of U.S. utility patent application Ser. No. 10/120,721, filed Apr. 11, 2002, now U.S. Pat. No. 6,654,629, which claims priority to U.S. Provisional Application No. 60/351,122, filed Jan. 23, 2002. This application also claims priority to U.S. Provisional Application No. 60/428,442, filed Nov. 22, 2002. These applications are hereby incorporated by reference in their entirety.

STATEMENT REGARDING FEDERALLY SPONSORED RESEARCH

Not Applicable

BACKGROUND OF THE INVENTION

1. Field of the Invention

This invention relates generally to ultrasound imaging systems, and more particularly to an ultrasound imaging system that can be delivered endoscopically.

2. Description of Related Art

Endoscopically deliverable ultrasound imaging systems are known in the art. Martin et al., U.S. Pat. No. 4,802,487, teaches an endoscopically deliverable ultrasound imaging system that includes an ultrasound probe mounted on the end of an endoscope that can be delivered by catheter. The axial or radial position of the probe is measured by a position transducer mounted on the endoscope adjacent the biopsy port from which the catheter extends. The output of the position measuring transducer is applied to the ultrasound imaging system so that the system provides an image of the tissue depth as a function of the position of the ultrasound probe. Additional examples of this technology are disclosed in Tanaka, U.S. Pat. No. 5,827,175, and U.S. Pat. No. 6,149,598.

Biomarkers are also disclosed in the prior art. The first class of prior art biomarkers include materials that have different ultrasound reflective properties and only remain in the body temporarily, eventually being reabsorbed by the body. An example of this technology is shown in Burbank et al., U.S. Pat. No. 6,161,034, assigned to SENOREX®, that teaches detectable markers that may be introduced by a cavity created by removal of a biopsy specimen to mark the location of the biopsy site so that it may be located in a subsequent medical/surgical procedure. The marker preferably includes gasses, saline solutions, or similar materials. The markers permit detection and location of the biopsy site at the first time point (e.g., up to 2 weeks) after introduction but do not interfere with imaging of tissues adjacent the biopsy site at a second time point.

Unger, U.S. Pat. No. 5,281,408 teaches a substantially homogeneous aqueous suspensions of low density microspheres which are presented as contrast media for imaging the gastrointestinal tract and other body cavities using computed tomography. In one embodiment, the low density microspheres are gas-filled. With computed tomography, the contrast media serve to change the relative density of certain areas within the gastrointestinal tract and other body cavities, and improve the overall diagnostic efficacy of this imaging method.

Unger, U.S. Pat. No. 5,334,381 teaches liposomes suitable as ultrasound contrast agents which contain media of various types including gases, gaseous precursors activated by pH, temperature or pressure, as well as other solid or liquid contrast enhancing agents. Methods of using and synthesizing the ultrasound contrast agents are also disclosed.

Klaveness et al., U.S. Pat. No. 5,676,925, teaches a gas containing, or gas generating, polymer microparticles or microballoons used as a contrast agent in ultrasound imaging.

Scarborough, U.S. Pat. No. 5,676,146 teaches a surgical implant containing a resorbable radiopaque marker that enables the position and/or orientation of the implant to be readily determined by x-ray or other radiographic technique following its surgical implantation into the body.

Smith, U.S. Pat. No. 4,909,250 teaches an animal identification system for swine or other livestock which employs an identification implant or pellet consisting of food grade material and imprinted with information to identify the source of the animal and its carcass after slaughter. The pellet is implanted under the hide or skin of the animal for purposes of identification. In the case of swine, the identification pellet is located in the fat layer of the shoulder area underneath its hide or skin. The pellet and the imprinted information consist of food grade material which is capable of being dissolved with the fat layer or disintegrated into cracklings in a rendering process. The pellet remains in the carcass after the animal is slaughtered until its removal to permit identification of the source of the animal. If the pellet is not removed, it is either dissolved with the fat of the animal or disintegrated into cracklings in the rendering process. Installation tools are disclosed for implanting the identification pellet in a horizontal or vertical orientation under the hide or skin of the animal.

Many references utilize metal reference markers that are then observed using x-rays. Example of these devices are as follows:

Kvavle et al., U.S. Pat. No. 4,007,732 describes X-ray techniques that are used to detect early evidence of breast cancer. When such evidence is found, a target is implanted in the suspect area while the patient is being x-rayed. The target has an attached line which leads from the target out through the skin of the patient. A biopsy is made with a cutting tool guided on the line attached to the target, thereby obtaining a biopsy specimen accurately centered on the suspect area.

Liprie, U.S. Pat. No. 5,282,781 teaches a composite source wire for use in treating malignant tumors within a patient's body by localized in vivo radiation with a radioactive source, via a catheter providing a path from a point external to the body to the tumor site. The source wire includes a thin continuous cylindrical flexible elongate stainless steel tube having encased therein a backbone wire running from its proximal end to a point short of its distal end to strengthen and enhance its flexibility, a cylindrical radioactive core adjacent to the distal end in abutting relation to the backbone wire, and a cylindrical plug at the distal end in abutting relation to the other end of the core, with the backbone wire, core and plug being tightly secured within the tube and the tube being securely enclosed about the plug with a tapered tip portion formed at that point. The source wire has an overall diameter sized to permit ease of movement through the catheter in advancement to the tumor site for the radiation treatment and to allow its retraction through the catheter from the point external to the body. The exterior surface of the tube is gold plated from its tip to the far end of the portion overlying the core. The source wire has an extremely small diameter (under 0.7 mm) and is sufficiently flexible that even in high radioactive dose sizes it is capable of passing through very narrow and even kinked catheters, making it useful for treating inoperable tumors such as common bile duct pancreatic cancer.

Hoffman et al., U.S. Pat. No. 4,693,237 describes marker members of radiopaque material in the form of bands each of a different geometric configuration which are sutured to the point at which a surgical graft to a blood vessel is made as in a coronary bypass operation. These ring or other shaped radiopaque members provide markers identifying the exact coronary blood vessel that the graft will lead to, each geometrical shape identifying a different coronary vessel bypassed, thus facilitating bypass graft catherization by identifying the entry point of any specific bypass graft.

Lam et al., 0 679 372 A2 teaches a radiopaque marker associated with a stent which is adapted to be implanted into a body lumen of a patient to maintain the patency thereof and a convenient and accurate method for affixing the radiopaque marker to the stent. The radiopaque marker defining an acceptable profile and capable of facilitating, under fluoroscopy, the identification of the position, diameter and length of a stent without obscuring the lesion being repaired and without impeding the deformation of an expendable stent.

Bahler et al., EP 0 146 699 A1 teaches implants consisting of contrast body and anchoring body fixed positionally secure in the bone with the aid of a structure of the anchoring body and thus form, in the bone, immovable reference points for the measurement of x-ray pictures.

Ellis, U.S. Pat. No. 5,636,255, describes a method and system for correlating accuracy of computer tomography (CT) image resolution. Small radio-opaque markers having a diameter less than one slice width of a CT scan are embedded in the object, such as a bony skeletal member, to be measured, the object is then CT scanned so that the radio-opaque markers appear in at two slices of the scan. The markers are also physically located by detecting them with a sensor, such as a positioning pointer. Also described is one form of marker comprising a tantalum sphere mounted in a ceramic, preferably alumina, pin.

Jensen et al., U.S. Pat. No. 6,181,960 B1, teaches a radiographic marker that is used to indicate a biopsy site and entry path. The marker has an arrow shape configuration with a shaft and a pair of limbs extending from the shaft at an angle of less than about 90 degrees. The tip of the arrow indicates the biopsy site and the shaft indicates the said entry path. The marker preferable is a single piece of wire, having a diameter of less than 0.010 inches, folded to four sections, to form the limbs and shaft of the arrow. Fibers can be affixed to the shaft to cause the marker to fibrose within the tissue. An introducing device, having a body and a hub, is used to insert the marker. A cannula, dimensioned to receive the body and hub of the introducing device, has a pair of receiving channels within the interior of the body to receive the limbs of the marker.

Jones, U.S. Pat. No. 4,202,349 describes a radiopaque blood vessel marker for attachment to the side wall portions of a blood vessel during, for example, a coronary by-pass operation. The markers in the preferred embodiment are flattened, oval-shaped radiopaque discs which are attached to the outer peripheral wall portion of the blood vessel at one hundred eighty degrees (180.degree.) with respect to one another (See FIG. 3). Each radiopaque marker can be comprised of a central imbedded element of radiopaque material such as tantalum which is surrounded by a suitable plastic or like resinous material which is inert and acceptable for use within the human body. During a coronary by-pass, for example, these markers could be attached by suturing or like means to the vein graft which is itself sutured into its new position during the by-pass operation. A fluoroscopic examination by a radiologist would reveal a desirable pulsation of the graft vessel in the form of the two attached markers as the radiopaque markers will constantly move (in and out) with respect to one another. Each marker is attached to the undulating wall portion of the vessel which is constantly moved when blood flow is passing through the graft as is desirable. In the event that complications arise, and the graft becomes clotted (stopping the flow of blood therethrough), a fluoroscopic examination will reveal that the radiopaque vessel markers do not move in and out with respect to one another but rather are stationary indicating a lack of undulation and a corresponding lack of blood flow.

Elliot et al., U.S. Pat. No. 4,041,931 relates to split ring markers fabricated in whole or in part from a radiopaque material, usually metal, having the terminal ends thereof and a medial portion formed to define eyelets by means of which said marker can be sutured to the tissue at the sight of an anastomosis to provide a visual indication of its location when examined fluoroscopically.

Foerster et al., U.S. Pat. No. 5,902,310 teaches an implantable marking device which is designed to percutaneously deliver permanent markers to desired tissue locations within a patient's body, even if the desired locations are laterally disposed relative to the distal end of the delivery device, as is the case for conduit or cavity walls. This provides several advantages to the physician in diagnosis and management of tissue abnormalities, such as a means of localization of a tissue abnormality for follow-up surgical treatment, and a means of tissue abnormality site identification for purposes of ongoing diagnostic follow-up. In one preferred construction, a radiographic clip is configured in the form of a surgical staple. A disposable tissue marker applier, which comprises a flexible tube, pull wire, and squeeze handle, is employed to advance and deploy the clip to a desired tissue location. Either a flexible or a rigid introducer is also provided for providing access to the site to be marked.

Morris, U.S. Pat. No. 4,331,654 describes a drug carrier formulation consisting of magnetically-localizable, biodegradable lipid microspheres.

Granov et al., U.S. Pat. No. 5,236,410 describes a method of treatment of a tumor comprising the steps of catheterization of the arterial vessel that feeds the tumor, and transcatheter administration of a suspension of magnetically hard ferromagnetic material in an oil solution of an oil-soluble antitumor substance with simultaneous application of local magnetic field onto the area of the tumor. After 1–3 days the tumor is subjected to ultrahigh radio frequency electromagnetic field or ultrasonic waves to produce heating of the tumor tissue to the temperature of 43.0.degree.–43.5.degree. C. for a period of 5–45 minutes.

Tournier et al., U.S. Pat. No. 5,668,490, teaches suspensions of either echogenic or magnetic particles in aqueous bioadhesive carriers that effectively improve imaging by echography, respectively NMRI, of the digestive tract. Affinity of the compositions for the gastric mucosa can be adapted to the needs by appropriately selecting the carrier in function to inherent bioadhesive capacity: this technique leads to improved visualization of selected portions of the lumen.

Additional patents of interest include Dowlatshahi, U.S. Pat. No. 5,853,366, which describes a marker element which is made of radiopaque material and includes at least two leg portions of approximately equal length connected at an angle relative to each other to form a generally V-shaped resilient member that is capable of being positioned wholly within the body of a patient. A localizing device and method using the marker element for marking a tissue mass of interest are also provided. The device and method include an elongate guide member, such as a cannula, having a first end that is inserted into the body so as to be directed toward a position proximate the tissue mass of interest and an opposite second end that extends from the body. A guide path extends between the first end and the second end of the guide member. The marker element is introduced into the second end of the guide member using a marker element dispenser and then urged along the guide path using a stylet or similar prodding member. The marker element collapses to a reduced size while being urged along the guide path, and substantially resumes its original V-shape upon discharge from the guide member so as to remain in a fixed position wholly within the body without irritating or traumatizing the surrounding tissue. A plurality of marker elements may be positioned in a similar manner to mark the tissue mass of interest.

Wichterle et al., U.S. Pat. No. 3,818,894 teaches an implant for surgical purposes which is especially useful for the operative treatment of the afflicted vocal cords, as well as to the method for its production. The implant is made from a physiologically inert material that swells in the presence of water, such as a synthetic cross-linked hydrophilic gel, and has in a dry state, when it is ready for use in an operation, the shape of a straight or bent stick provided with a sharp, pointed tip. The implant body except the tip may contain physiologically inert plasticizers.

Tucci, U.S. Pat. No. 4,545,367 teaches a detachable balloon catheter assembly which comprises a balloon and sealing valve assembly including a sealing valve being formed of a resilient material having an elongate passageway extending therethrough and being mounted in a sleeve, an inflatable balloon having a mouth portion which is bonded to the sealing valve, and a small diameter cannula having a distal end which extends through the passageway in the sealing valve. The small diameter cannula includes a connector terminal on the proximal end which is adapted to be coupled to a source of fluid pressure. The passageway in the sealing valve takes the form of an elongate slit prior to insertion of the small diameter cannula through the passageway, and upon insertion of the cannula through the passageway, the passageway takes the form of a cylindrical aperture which is in fluid-tight engagement with the outer surface of the cannula while allowing the cannula to easily slide through the passageway. When the balloon is inflated to a desired size, the cannula may be withdrawn from the passageway in the sealing valve thereby causing the passageway to revert to the slit configuration in order to provide a fluid-tight seal for the inflated balloon. In one embodiment, a piston is mounted on the small diameter cannula and an aperture extends through the side wall of the cannula so that a burst of fluid pressure may be applied to the piston causing it to be driven away from the sealing valve to drive the cannula out of engagement with the sealing valve for detachment of the cannula from the inflated sealed balloon.

Barlow et al., U.S. Pat. No. 5,422,730 describes a method and apparatus for optical detection and imaging of regional circulatory flow in biological tissues for research purposes. An animal or plant organ is perfused with a saline suspension of colored and/or fluorescent microspheres. The organ is excised and fixed in the form of a specimen block for mounting in a microtome or other suitable apparatus. Under automatic control of a microcomputer equipped with a frame grabber, a surface layer of the block is removed, the resulting new exposed surface of the block receives a flash of illumination from a light source, and light reflected by colored microspheres or, alternatively, light emitted by fluorescent microspheres, is detected by a CCD video camera aimed at the block. Also under microcomputer control, light filters having suitable light bandpasses are interposed between the light sources and the block, and between the block and the camera. Video signals are converted by the microcomputer into position coordinates with associated optical intensities from which regional circulatory flow is computed and displayed on a monitor.

Other references of interest include Leeb et al., U.S. Pat. No. 5,643,246, Ahmed, U.S. Pat. No. 4,647,480, Klaveness et al., U.S. Pat. No. 5,676,925, Miller et al., U.S. Pat. No. 6,481,685, Chapelon et al., WO 93/14712, WO 96/08208, and Foerster et al., WO 98/06346.

The above-described references are hereby incorporated by reference in full.

SUMMARY OF THE INVENTION

The present invention teaches certain benefits in construction and use which give rise to the objectives described below.

The present invention provides an ultrasound imaging system having an ultrasound probe adapted to be placed in an instrument working channel of an endoscope. The ultrasound probe includes a probe housing; an ultrasound transducer mounted within the probe housing; and an elongate flexible cord extending from the probe housing, the elongate flexible cord being adapted to fit through the instrument working channel of the endoscope and operably connect the ultrasound transducer with a computer; and a biomarker mounted on the ultrasound probe. The biomarker includes a MEMS housing constructed of a biocompatible material.

A primary objective of the present invention is to provide an ultrasound imaging system having advantages not taught by the prior art.

Another objective is to provide an ultrasound imaging system that includes a biomarker that includes a MEMS housing constructed of a biocompatible material.

Other features and advantages of the present invention will become apparent from the following more detailed description, taken In conjunction with the accompanying drawings, which illustrate, by way of example, the principles of the invention.

BRIEF DESCRIPTION OF THE DRAWING

The accompanying drawings illustrate the present invention. In such drawings:

FIG. 18 is a perspective view of an insertion device adapted for use with the ultrasound imaging marker;

FIG. 19 is a perspective view of an ejection device within the insertion device for ejecting the ultrasound imaging marker;

FIG. 20 is a side elevational sectional view of a cannula of the insertion device illustrating how three ultrasound imaging markers can be positioned within the insertion device;

FIG. 21 is a side elevational sectional view of the insertion device being used to insert two of the ultrasound imaging markers adjacent a location, a tumor, in the mammalian body;

DETAILED DESCRIPTION OF THE INVENTION

Figure 1:
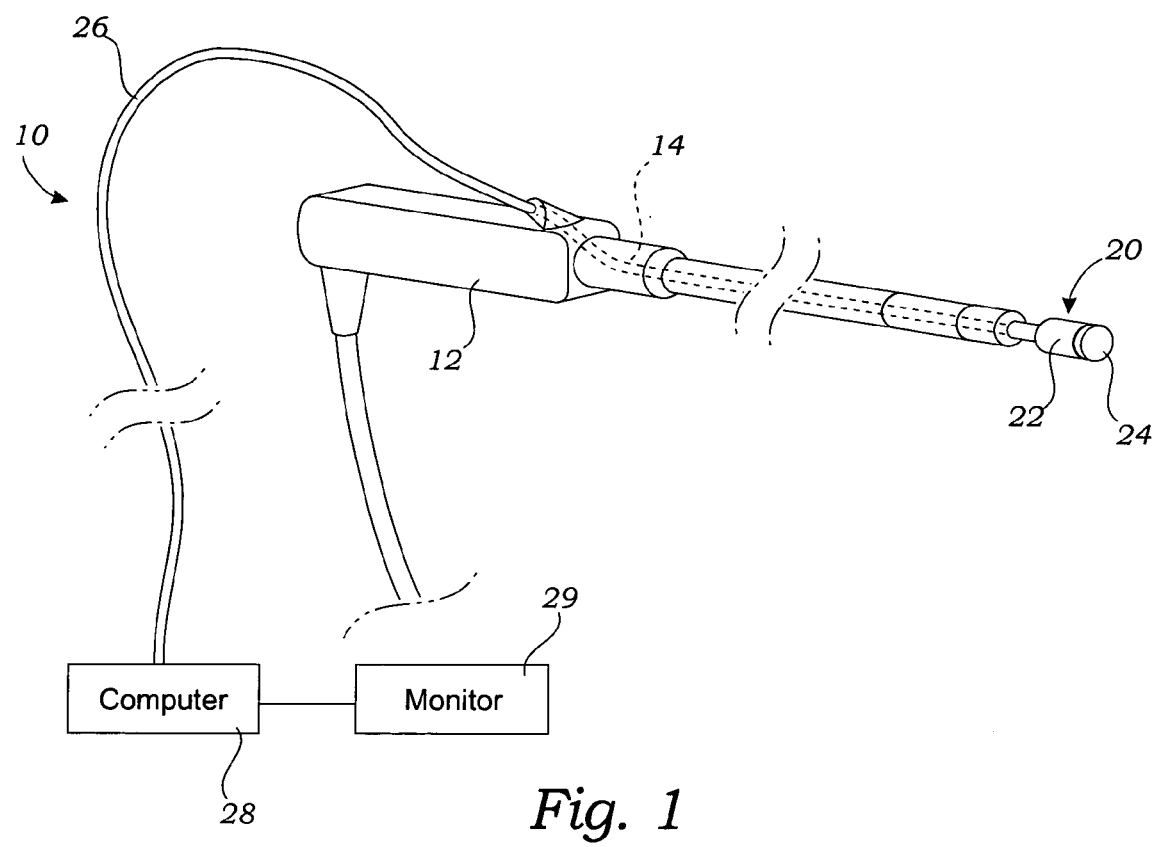
FIG. 1 is a perspective view of an ultrasound probe operably positioned through an endoscope.

The above-described drawing figures illustrate the invention, an ultrasound imaging system 10 that can be delivered through an endoscope 12. As shown in FIG. 1, the ultrasound imaging system 10 includes an ultrasound probe 20 adapted to be placed in an instrument working channel 14 of the endoscope 12. The ultrasound probe 20 includes a probe housing 22; an ultrasound transducer 24 mounted within the probe housing 22; and an elongate flexible cord 26 extending from the probe housing 22. The elongate flexible cord 26 is adapted to fit through the instrument working channel 14 of the endoscope 12 and operably connect the ultrasound transducer 24 with a computer 28.

As shown in FIG. 1, the computer 28 is operably attached to a monitor 29 for displaying the images generated by the ultrasound imaging system 10. As used in this application, the term "monitor" 29 includes a standard CRT computer monitor 29, an LCD or plasma display, a projection device, a television, or any other similar display device.

Ultrasound Transducer

Figure 2:
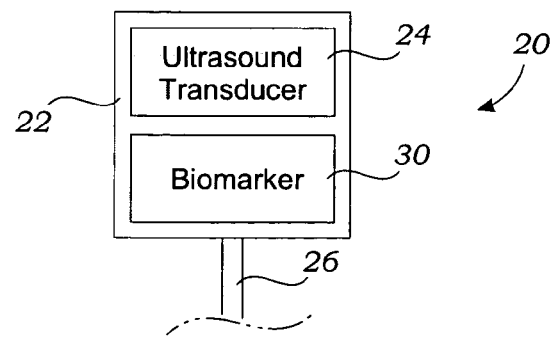
FIG. 2 is a block diagram of one embodiment of the ultrasound probe wherein a probe housing includes a biomarker.
Figure 3:
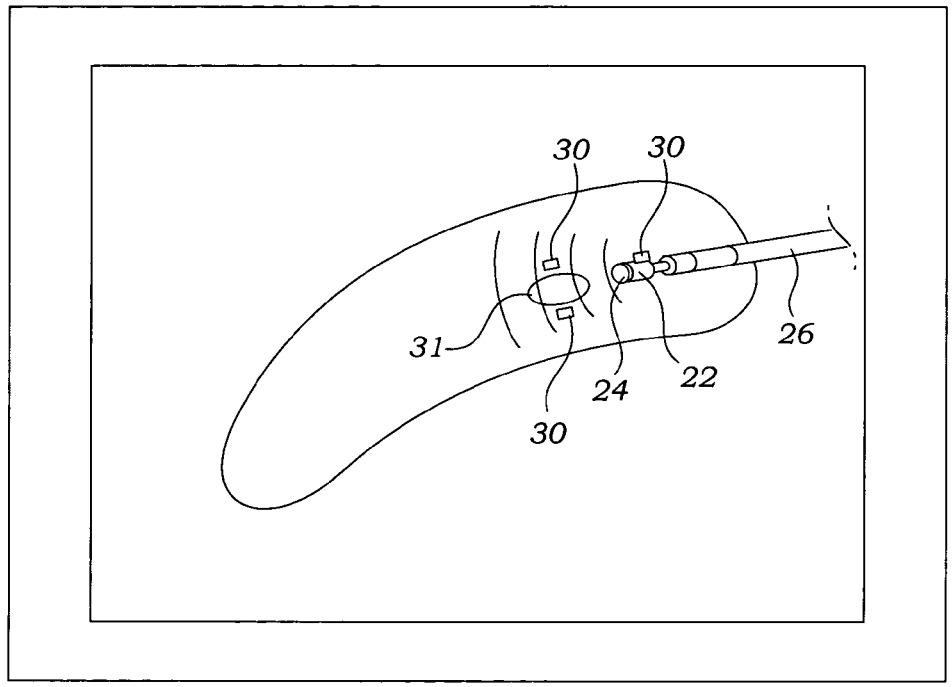
FIG. 3 is a front elevational view of a monitor displaying the ultrasound probe being used to investigate a suspected tumor previously marked with a pair of biomarkers.

A first embodiment of the ultrasound probe 20 is shown in FIGS. 2 and 3. In this embodiment, the probe housing 22 supports the ultrasound transducer 24 for use; and the robe housing 22 also includes a biomarker 30 mounted either inside of or on the outer surface of the probe housing 22. As described below, the biomarker 30 is used to track the position of the probe housing 22 within the patient's body. It is also possible to use a plurality of the biomarkers 30 to more accurately monitor the position of the ultrasound probe 20, and the elongate flexible cord 26.

As shown in FIG. 3, the ultrasound probe 20 can be inserted into the patient's body for analyzing an area of interest, such as a suspected tumor 31. The ultrasound probe 20 is particularly well adapted to investigating the vascular system, the gastrointestinal system, and the like. In this particular embodiment, the ultrasound probe 20 is being used to investigate a suspected tumor 31 in a liver. A pair of the biomarkers 30 are shown placed on the perimeter of the suspected tumor 31. A description of how the biomarkers 30 are inserted is provided below.

Figure 22:
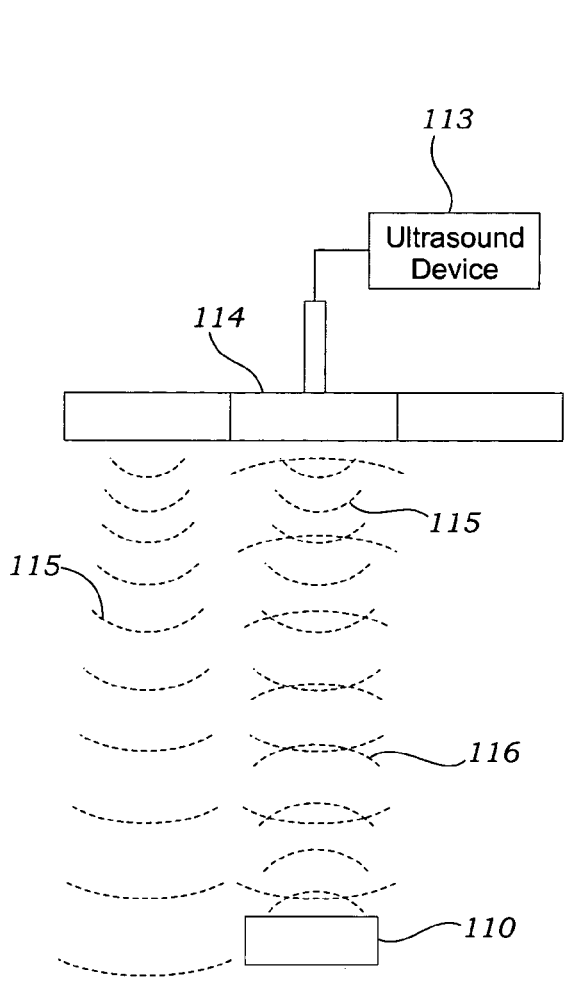
FIG. 22 is a side elevational view illustrating how a transducer of an ultrasound device is used to project an ultrasound wave onto the ultrasound imaging marker, and how the ultrasound imaging marker generates reflected waves that are detected by the transducer.
Figure 23:
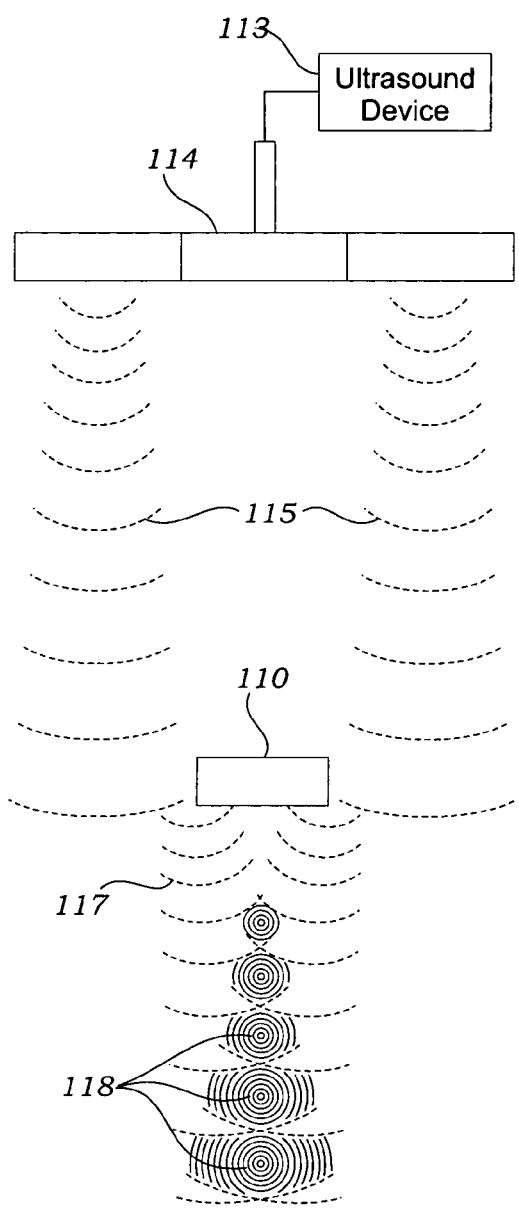
FIG. 23 is a side elevational view illustrating how the ultrasound imaging marker generates reflected and refracted waves that form a moiré pattern that is detected by the transducer.

An ultrasound device outside the patient's body, as shown in FIGS. 22–23, is used to locate the suspected tumor 31 using the pair of biomarkers 30. The second ultrasound device also displays the location of the ultrasound probe 20, due to or highlighted by the biomarker 30 located on or within the probe housing 22. A display, shown in FIG. 3, illustrates the movement of the ultrasound probe 20 relative to the patient's body and relative to the suspected tumor 31, and facilitates the proper placement of the ultrasound probe 20.

In at least some embodiments, the biomarker 30 includes a power generation system (not shown) that derives power from the ultrasonic signal. One benefit of mounting the ultrasound transducer 24 on the probe housing 22 and moving the ultrasound transducer 24 directly adjacent the area of interest is that the ultrasound transducer 24 can then be used to more efficiently power the biomarker 30. Placing the probe housing 22 adjacent the biomarker 30 located at the area of interest amplifies the power induced, thereby enabling secondary features of the biomarker 30, such as the function of a CPU or similar device without the use of an implanted battery.

The probe housing 22 is particularly suited for endovascular use, and can be inserted into and through either arteries and/or veins using techniques that are well known in the art. Endovascular positioning enables the surgeon to get an ultrasound picture of a site of interest with minimal invasion of the patient's body.

Stent Insertion Device

Figure 5:
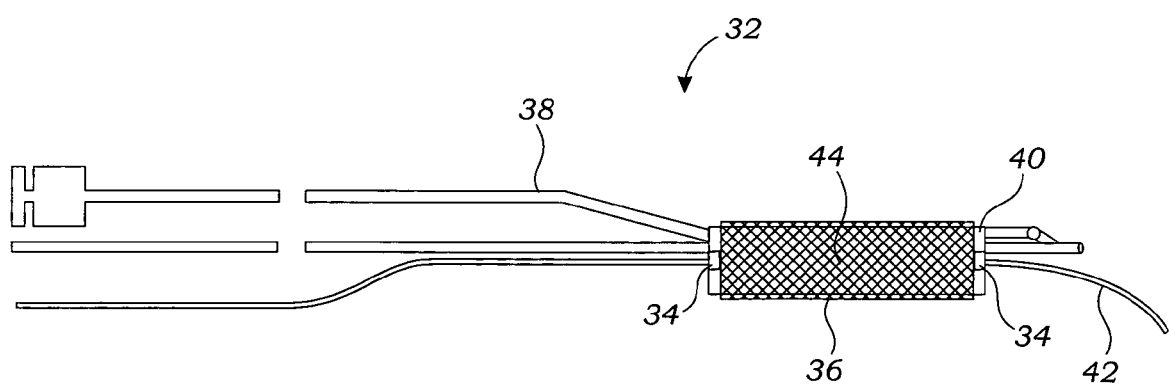
FIG. 5 is a side elevational view of the stent insertion device.
Figure 4:
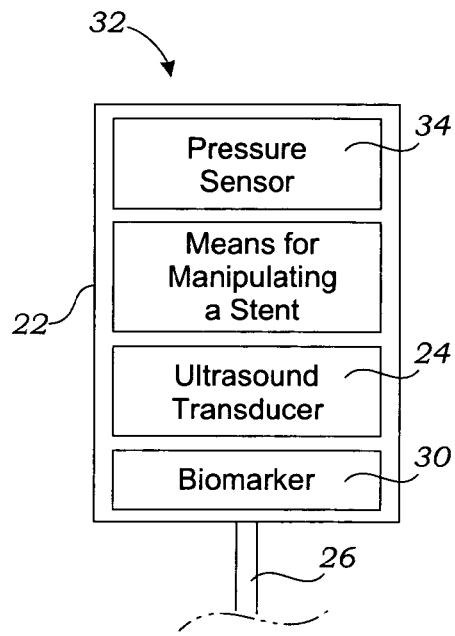
FIG. 4 is a block diagram of an embodiment wherein the probe housing includes a stent insertion device.

In an alternative embodiment, as shown in FIGS. 4 and 5, the probe housing 22 includes a pressure sensor 34 in addition to the ultrasound transducer 24. The pressure sensor 34 is used during the operation to monitor 29 the pressure of the blood in the surrounding artery or vein during a surgical procedure. As shown in FIG. 5, the probe housing 22, adapted for inserting a stent 36, includes a means for manipulating a stent 36. The means for manipulating the stent 36 may include the elements shown in FIG. 5, including an elongate flexible advancement member 38 that terminates in a tubular tracking member 40 that is adapted to be slidably advanced over a guidewire 42. In this embodiment, the means for manipulating further includes an inflatable balloon 44 mounted under the stent 36 for expanding the stent 36 once it has been properly positioned.

Examples of prior art stent insertion devices are described in Solar et al., U.S. Pat. No. 6,447,501 B1, and Lashinski et al., U.S. Pat. No. 6,071,285, both of which are hereby incorporated by reference in full. Of course, those skilled in the art might adapt another design that is well known in the art, and these alternative embodiments should be considered within the scope of the present invention.

The probe housing 22 may be inserted into the heart of a patient (not shown) until the stent 36 is properly positioned. The surgeon is able to use the pressure sensor 34 to monitor the pressure within the surrounding blood to make sure the procedure proceeds as planned. If the pressure either rises or drops in an unexpected manner, the surgeon can immediately take corrective action to avoid or minimize damage to the patent's heart tissue. Once the stent 36 is positioned, the inflatable balloon 44 is used to expand the stent 36 into its final position and configuration. In general, the placement and expansion of the stent 36 are well known in the art, and are therefore not described in greater detail herein.

Ablation Device

Figure 7:
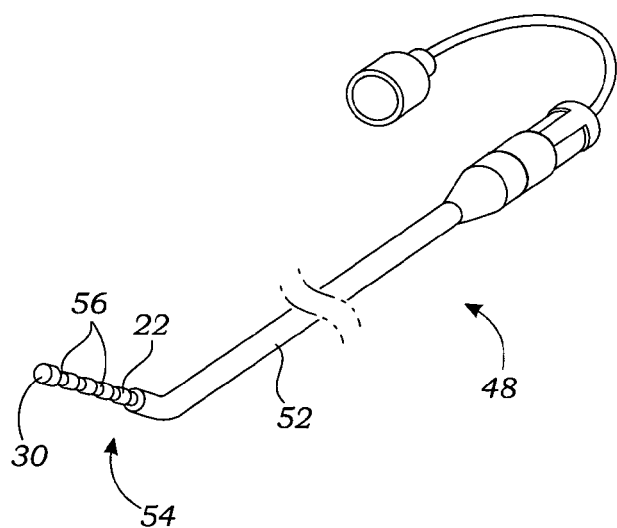
FIG. 7 is a perspective view thereof.
Figure 6:
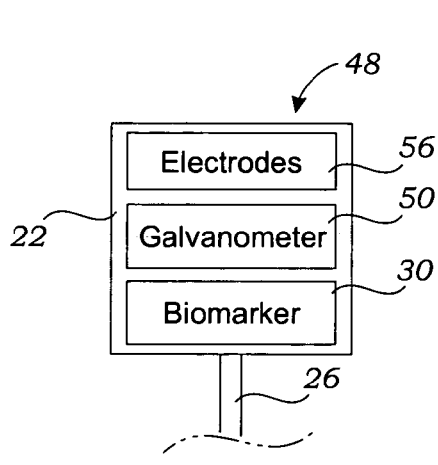
FIG. 6 is a block diagram of an embodiment wherein the probe housing includes an ablation device including electrodes and a galvanometer.

In another alternative embodiment, as shown in FIGS. 6 and 7, the probe housing 22 includes an ablation device 48, a galvanometer 50, and the biomarker 30. The probe housing 22 of this embodiment is adapted to be used to treat a condition known as atrial fibrillation The galvanometer 50 is used by a surgeon to measure electric impulses within a patient's heart (not shown). The ablation device 48 can include a monopolar, bipolar, cryosurgical, or similar type of energy system, as is known in the art. When a problem area is found that does not signal properly, the ablation device 48 is used to ablate the problem area so that the incorrect signals are eliminated and cardioversion occurs.

As shown in FIG. 7, the probe housing 22 preferably includes a flexible shaft 52 that is adapted to be inserted into the patient's arteries or veins using the endoscope 12. The flexible shaft 52 extends to a flexible tip 54 having one or more electrodes 56. The flexible tip 54 may include a deflection mechanism (not shown) for enabling the surgeon to manipulate the position of the flexible tip 54. The deflection mechanism can include any of the known mechanisms, such as a combination of a pull wire and a flat spring (not shown). A similar device is shown in Carner et al., U.S. Pat. No. 6,332,881 B1, hereby incorporated by reference in full.

As before, the biomarker 30 is used to locate and track the position of the probe housing 22. In the preferred embodiment, the biomarker 30 is mounted in or adjacent to the flexible tip 54. A plurality of the biomarkers 30 may be mounted at various points along the length of the probe housing 22 for the purpose of better tracking the position of the probe housing 22, especially the flexible tip 54, during the course of the operation. As described below, the plurality of the biomarkers 30 may also be implanted within the patient's body and/or attached to implanted devices.

Various alternative embodiments of the ablation device 48 can also be used, including Sutton, U.S. Pat. No. 6,443,950 B1, which is also incorporated by reference in full. These and other alternative embodiments of the ablation device 48, which is known in the art, could also be adapted for use according to the teachings of the present invention, and should therefore be considered within the scope of the present invention.

In use, the probe housing 22 is inserted into the body of the patient using the endoscope 12, as is generally well known in the art. The surgeon is able to use a conventional ultrasound device to track the flexible tip 54 of the probe housing 22 because of the biomarkers 30 mounted therein.

Once the probe housing 22 is in place, the galvanometer 50 is used to measure the electrical impulses within the heart of the patient (not shown) to determine the location of the problem areas, as described above. Once located, the flexible tip 54 is manipulated by the surgeon until the one or more electrodes 56 are positioned in contact with the problem area. The electrodes 56 then function to ablate the problem area, thereby removing the errant or asynchronous electrical impulses.

Biomarker

The biomarker 30 described above is used in conjunction with an image-guided system to enable a surgeon to quickly and easily find the location without requiring extensive x-rays or the use of expensive and cumbersome equipment. As shown in FIGS. 22–23, the biomarker 30 is designed for use in conjunction with ultrasound device 113 having a transducer 114, although some embodiments are adapted to also work in x-rays and other related imaging systems. The ultrasound device 113 typically operates in the 3.5–20.0 megahertz range. The image generated by the ultrasound device 113 can be displayed on the monitor 29, as shown in FIG. 3. Many different embodiments of the biomarker 30 can be used, two of the preferred embodiments being described below.

First Embodiment of the Biomarker

Figure 8:
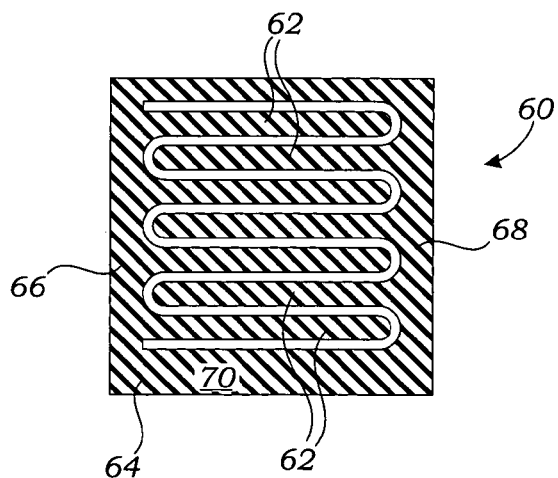
FIG. 8 is a top plan view of a first embodiment of the biomarker.

In a first embodiment of the biomarker 30, shown in FIG. 8, the biomarker 30 includes a MEMS housing 60 and a signaling means for receiving an excitation signal and returning a return signal. In one embodiment, the MEMS housing 60 is a silicon chip that includes a biocompatible outer surface (not shown) such as paralyne or other coating well known in the art. The MEMS housing 60 can also be constructed solely of a biocompatible material, and therefore not require the outer surface. The MEMS housing 60 is preferably approximately 1–2 mm in any dimension, or smaller, so as to minimize its interference with the surgical procedure.

The signaling means includes a plurality of wave-guide features 62 that are integral with the MEMS housing 60 and adapted to resonate when struck by an excitation signal that is frequency matched or is of a given frequency and return a return signal. It is possible to manufacture the biomarker 30 with such a small housing using MEMS manufacturing techniques that are known to those skilled in the art. Since MEMS manufacturing techniques are well known in the art, they are not described herein in greater detail.

In the preferred embodiment, the MEMS housing 60 includes a dielectric base 64 that includes two opposing sides 66 and 68 extending from the dielectric base 64. In this embodiment, the plurality of wave-guide features 62 are a plurality of wave-guide rods that are integral with and extend from the dielectric base 64. As shown in FIG. 8, the plurality of wave-guide rods 62 are disposed on a plane and in a parallel orientation, and each of the plurality of wave-guide rods 62 extend from, in alternating order, one of the two opposing sides 66 and 68, such that each of the plurality of wave-guide rods 62 overlaps those adjacent, between the two opposing sides.

While we state that the plurality of wave-guide rods 62 are disposed on a plane and in a parallel orientation, this does not mean that they are limited to precisely this orientation, but only that the axis of each of the plurality of wave-guide rods 62 is generally oriented in this fashion with respect to at least one of the others, plus or minus 8 degrees. Furthermore, since this is only the most preferred embodiment, other orientations and configurations should be considered within the scope of the invention.

The surface 70 of the dielectric base 64 can be welded or bonded to one of the surgical instruments described herein to attach the biomarker 30 thereto. Details of the attachment are described in greater detail herein.

Second Embodiment of the Biomarker

As shown in FIGS. 9–14, in other embodiments the biomarker 30 is an ultrasound imaging marker 110 that includes a marker body 120 constructed of an ultrasound resonant material such as plastic, vinyl, silicon, glass, copolymer, or equivalent material. In one embodiment, the ultrasound resonant material is constructed of bioabsorbable polymer of similar material. The marker body 120 has an interior surface 122 and an exterior surface 124. The interior surface 122 defines a resonant pocket 126. A metallic resonant layer 128 covers at least a portion of the interior surface 122. The combination of the resonant pocket 126 and the metallic resonant layer 128 function to reflect, refract, or deflect the ultrasound waves 115, as shown in FIGS. 22–23, thereby making the location 111 readily apparent to a search by the ultrasound device 113. This construction makes the ultrasound imaging marker 110 an effective marker despite its small size, which is preferably less than 5 mm in length.

Figure 9:
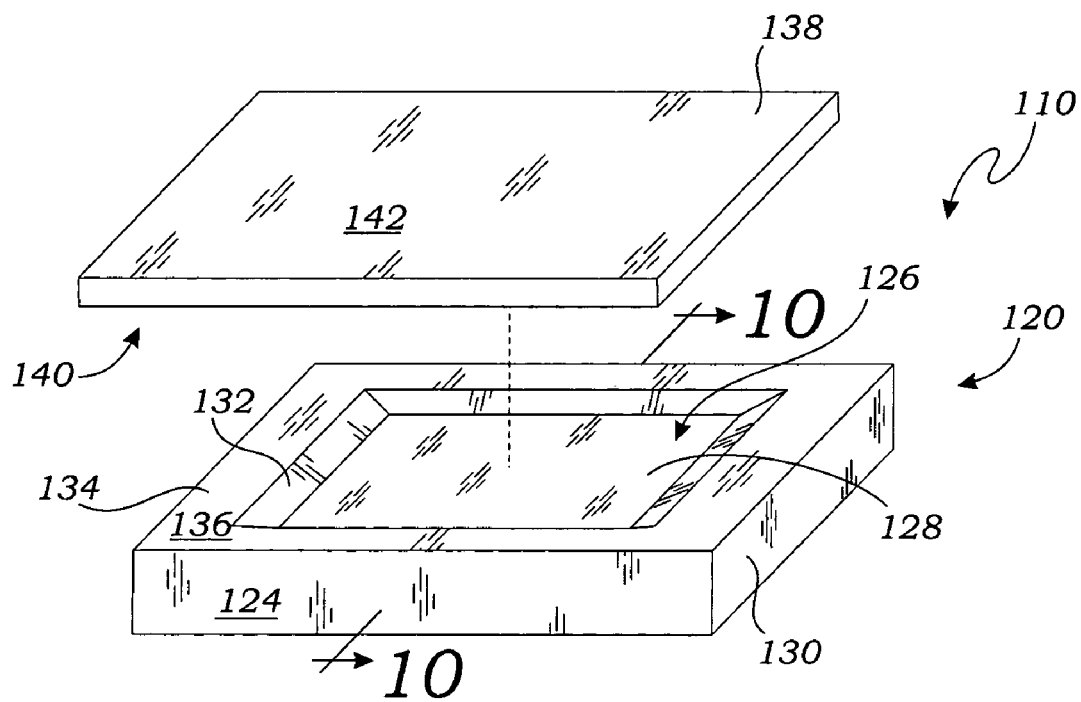
FIG. 9 is an exploded perspective view of another embodiment of an ultrasound imaging marker.
Figure 10:
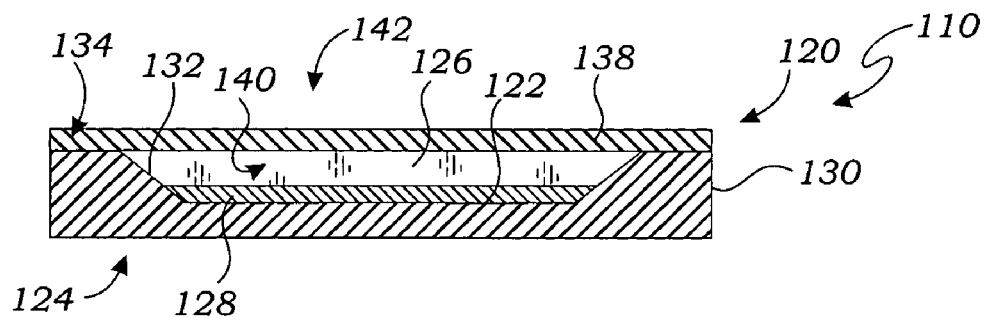
FIG. 10 is a sectional view thereof taken along line 10—10 in FIG. 9.
Figure 11:
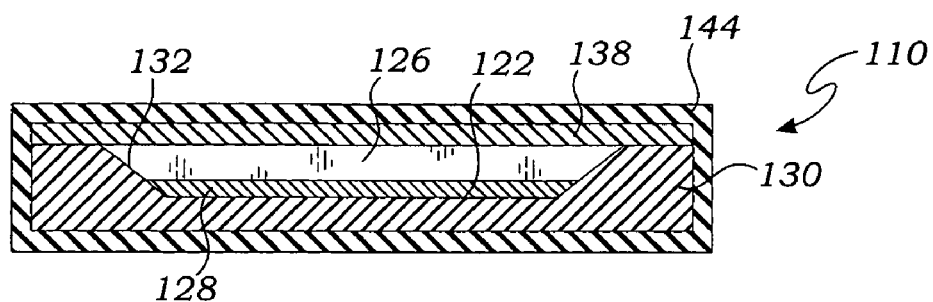
FIG. 11 is a sectional view thereof illustrating the addition of a biocompatible coating around the ultrasound imaging marker.

In a first embodiment, as shown in FIGS. 9–11, the marker body 120 is constructed of a marker base 130 and a cap 138. The marker base 130 has an angled surface 132, a perimeter lip 134, and an exterior surface 124 in addition to the interior surface 122. The perimeter lip 134 defines an opening to the resonant pocket 126, the resonant pocket 126 being bounded by the interior surface 122 and the angled surface 132. The cap 138 functions to seal the resonant pocket 126.

To enhance the visibility of the resonant pocket 126, the interior surface 122 is preferably generally planar, although this is not required for the function of the ultrasound imaging marker 110. Due to the difference in the echogenicity of the air in the resonant pocket 126 and the ultrasound resonant material of the marker base 130, the interior surface 122 functions to reflect and refract ultrasound waves 115. As shown in FIG. 22, reflected waves 116 from the ultrasound imaging marker 110 can be detected using a transducer 114 of the ultrasound device 113.

As shown in FIG. 9, the angled surface 132 bounds the interior surface 122 and connects the interior surface 122 with the perimeter lip 134. The angled surface 132 is preferably disposed on a plane that is at an angle of between 120–140 degrees with respect to the plane of the interior surface 122, more preferably at an angle of between 123–130 degrees, and most preferably at an angle of approximately 126 degrees. As shown in FIG. 23, the angled surface 132 functions to refract the ultrasound waves 115 to form refracted waves 117. The refracted waves 117 form a moiré pattern 118 that is readily discernable on the ultrasound device 113.

The moiré pattern 118, sometimes known as a "waterfall effect," facilitates locating the ultrasound imaging marker 110 using the ultrasound device 113.

As shown in FIGS. 9–10, the cap 138 has an inner cap surface 140 and an exterior cap surface 142. The perimeter lip 134 further has a lip surface 36. The lip surface 136 is preferably disposed on a plane that is generally parallel to the plane of the interior surface 122. The inner cap surface 140 is mounted on the perimeter lip 134 and bonded to the lip surface 136 of the marker base 130 to close the opening of the resonant pocket 126.

In one embodiment, in which the marker base 130 and the cap 138 are made of silicon, the silicon components naturally bond together so that the inner cap surface 140 adheres to the lip surface 136 of the marker base 130. In alternative embodiments, an adhesive can be used to bond the inner cap surface 140 and the lip surface 136. In the one embodiment in which the marker base 130 is made of silicon, the interior surface 122 is preferably etched from a silicon wafer using KOH etching, a technique well known in the art and therefore not described in greater detail herein.

As shown in FIG. 11, the cap 138 and the marker base 130 are preferably coated with a biocompatible coating 144 or sealant, such as paralyne, to further prevent leakage into the resonant pocket 126. The biocompatible coating 144 can also be used to coat the cap 138 and the marker base 130 if either of the above elements are not suitably biocompatible. Since the marker body 120 is preferably biocompatible, however, the biocompatible coating 144 is not generally required for biocompatibility.

Figure 12:
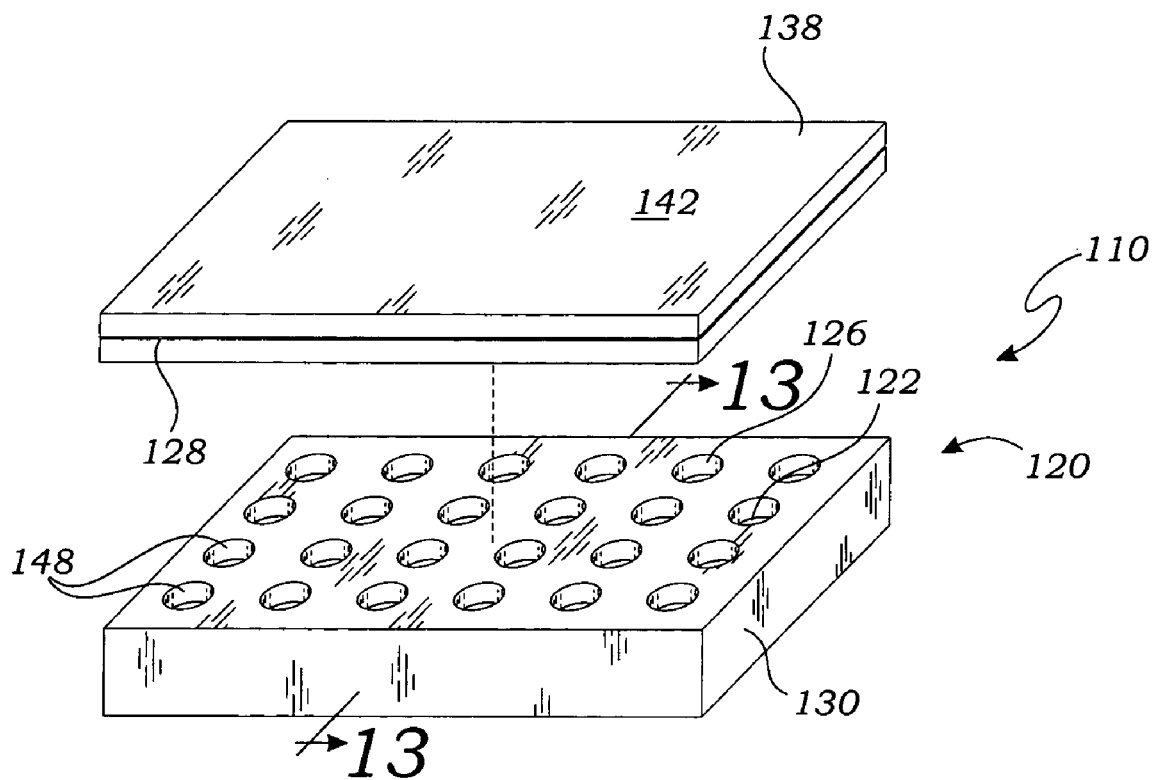
FIG. 12 is an exploded perspective view of yet another embodiment of the ultrasound imaging marker.
Figure 13:
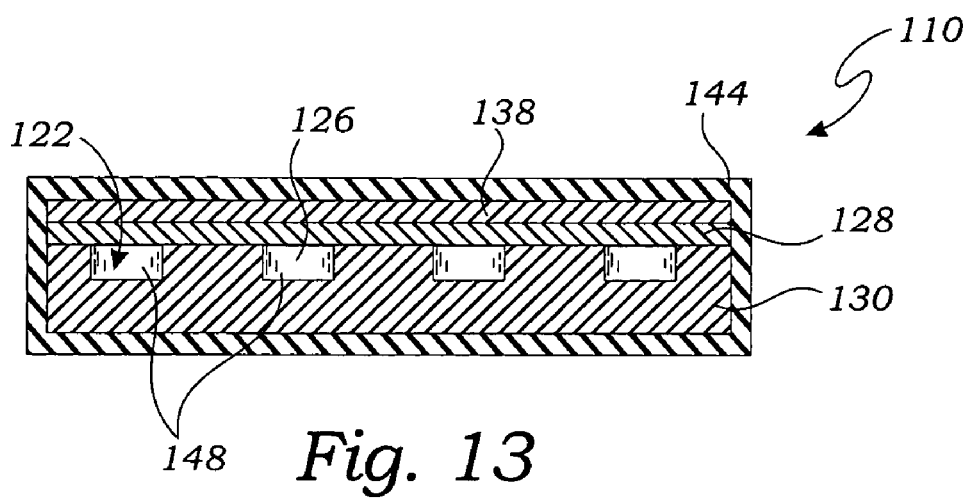
FIG. 13 is a sectional view thereof taken along line 13—13 in FIG. 12 and further including a biocompatible coating.

In one embodiment, shown in FIG. 10, the interior surface 122 is preferably coated with a metallic resonant layer 128 such as alumina or gold. The metallic resonant layer 128 can be formed by sputtering alumina, which is inexpensive, onto the interior surface 122; however, gold or other metals can also be used, especially in applications where higher costs are not a barrier. Also, other deposition or layering techniques can be used by those skilled in the art, and such alternative techniques should be considered within the scope of the present invention. In addition to enhancing the ultrasound signal, the metallic resonant layer 128 serves to assist in the identification of the CHIP when using x-ray or similar In a second embodiment, as shown in FIGS. 12–13, the interior surface 122 is formed by a plurality of bores 148. The plurality of bores 148 are preferably evenly spaced in a grid pattern, and each of the plurality of bores 148 is preferably between 50–150 microns deep, more preferably between 80–120 microns deep, and most preferably approximately 100 microns deep. In this embodiment, the metallic resonant layer 128 is preferably formed on the interior cap surface of the cap 138 so that when the cap 138 is bonded to the marker base 130, the metallic resonant layer 128 is properly positioned as part of the resonant pocket 126. While the two embodiments described illustrate the preferred methods of forming the resonant pocket 126, alternative arrangements can be devised by those skilled in the art, and should be considered within the scope of the claimed invention.

Figure 14:
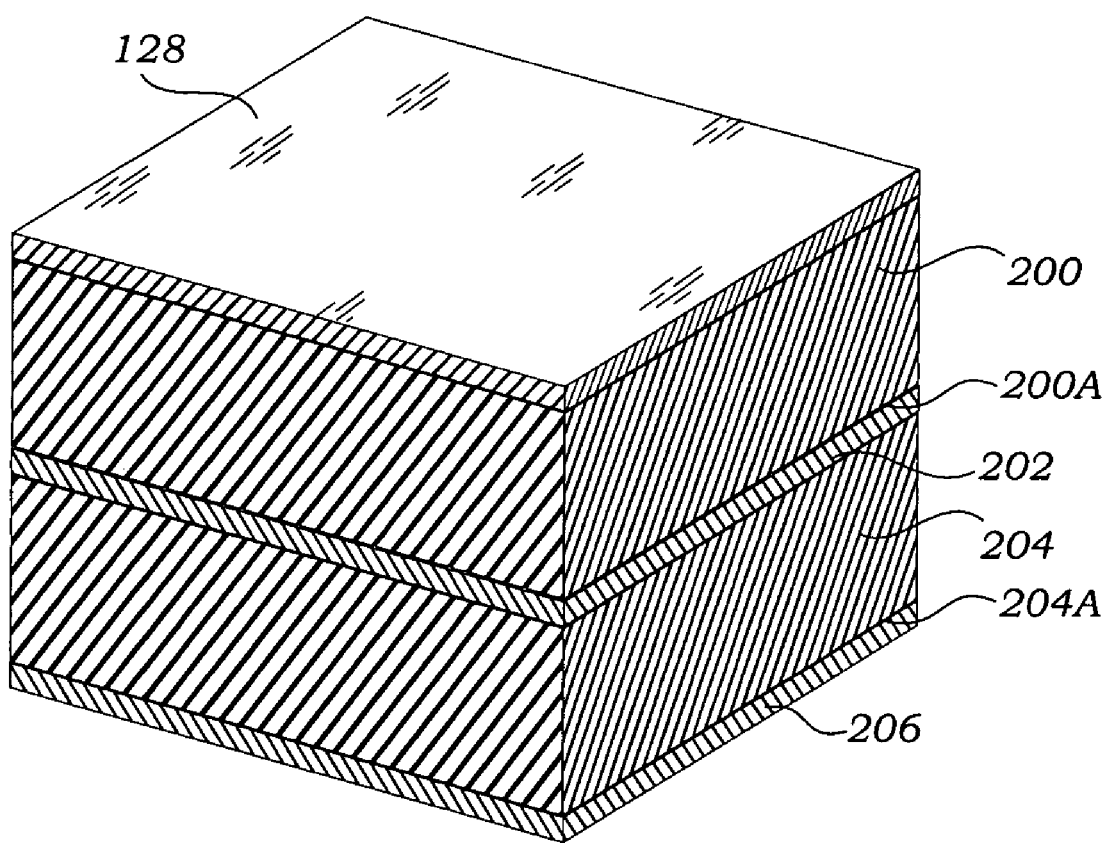
FIG. 14 is a sectional view of another embodiment of the ultrasound imaging marker.

In another embodiment, as shown in FIG. 14, the ultrasound imaging marker 110 includes a marker body 120 constructed of a first silicon layer 200 coated upon one side with the metallic resonant layer 128, and upon the opposing side having a first silicon oxide layer 202. In one embodiment, the marker body 120 further includes a second silicon layer 204 that is sandwiched between the first silicon oxide layer 202 and a second silicon oxide layer 206. In this embodiment, the metallic resonant layer 128 includes both alumina and gold. Each of the first and second silicon layers 200 and 204 are etched using a well known etching technique such as chemical (KOH) etching or similar method, to form roughened surfaces 200A and 204A, that have various small pits and irregularities. Upon exposure to air, the roughened surfaces 200A and 204A form the first and second silicon oxide layers 202 and 206. It has been found that merely providing a roughened surface serves to form the resonant pocket 126 without specifically etching the plurality of bores 148. While this embodiment is not as effective as the technique described above, it is still fairly effective and much cheaper to manufacture. The marker body 120 in this embodiment is typically about 1 mm wide and 0.5 mm thick, although the size can vary depending upon the requirements of the user.

Means for Mounting

The dielectric base preferably includes a means for mounting the biomarker 30 on a surgical device such as described above. The means for mounting may include bonding the dielectric base to the probe housing 22 using any bonding or other attachment mechanisms known in the art. In a typical embodiment, a bottom surface of the dielectric base is bonded, welded, or otherwise affixed or attached to the surgical device. The biomarker 30 may also be bonded or otherwise affixed to an intermediary attachment element (not shown) that is then attached, either fixedly or removably, to the surgical device.

Figure 15:
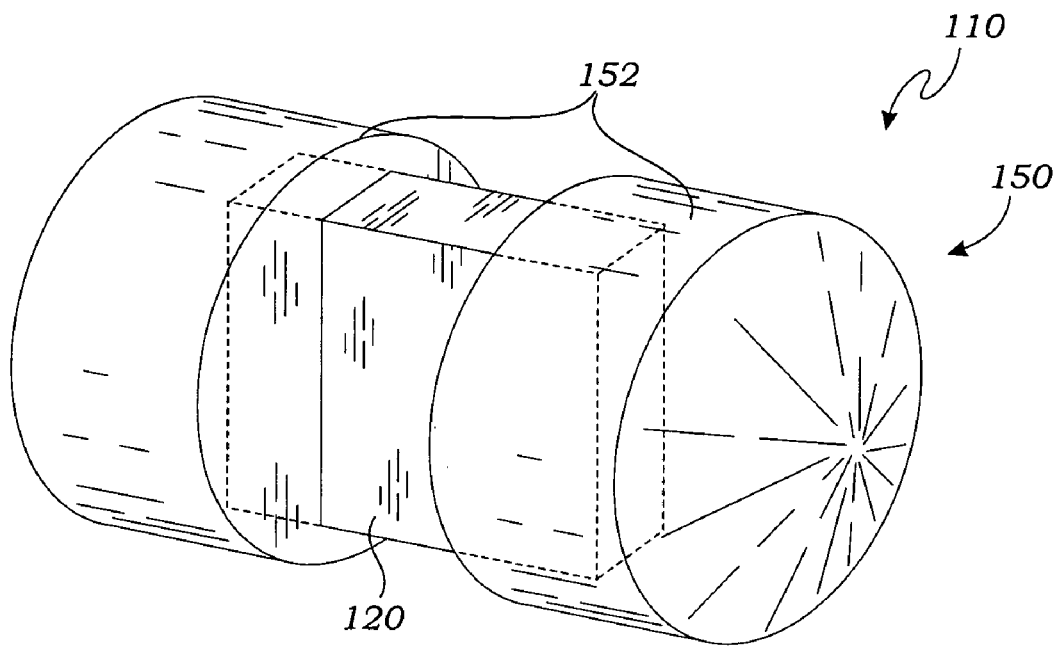
FIG. 15 is a perspective view of the ultrasound imaging marker including a pair of positioning end caps that function to prevent migration of the ultrasound imaging marker within a mammalian body.
Figure 16:
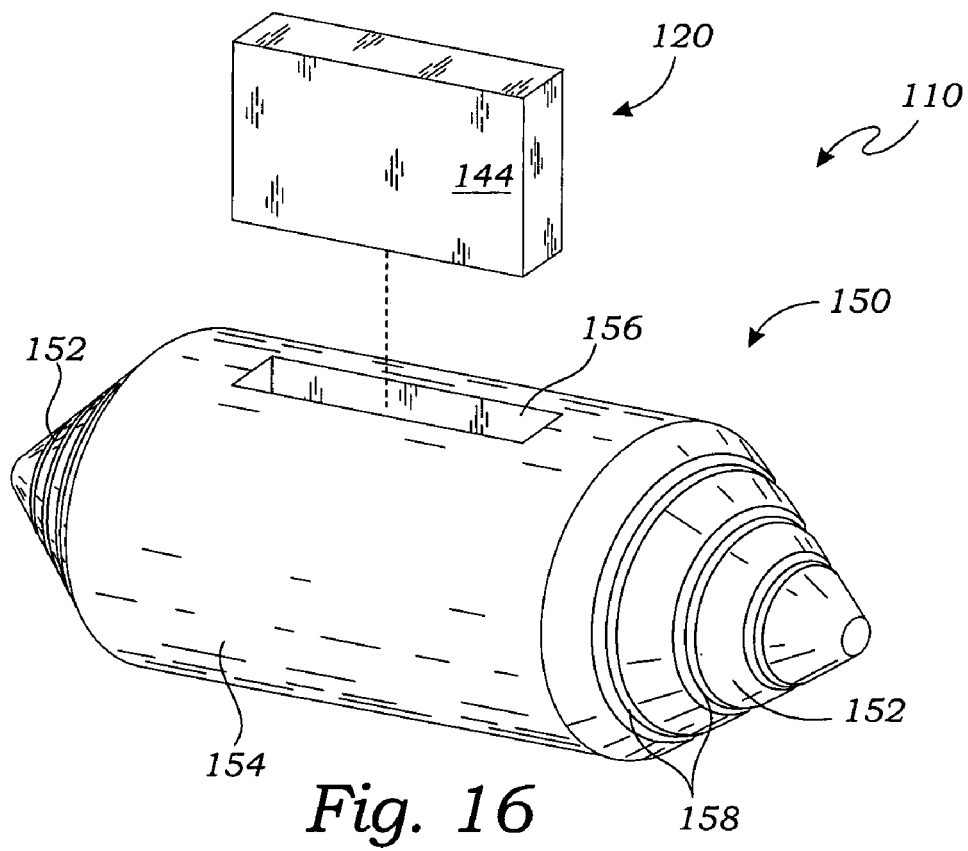
FIG. 16 is a perspective view of the ultrasound imaging marker being inserted into a slot of a central body, the central body having a pair of positioning end caps that likewise function to prevent migration of the ultrasound imaging marker.

In an alternative embodiment, the ultrasound imaging marker 110 is associated with a means for preventing migration 150 of the ultrasound imaging marker 110 within the mammalian body 112. As shown in FIGS. 15–16, the means for preventing migration 150 includes at least one positioning end cap 152 operably attached to the ultrasound imaging marker 110. The at least one positioning end cap 152 functions to properly position the ultrasound imaging marker 110 within soft tissue of the mammalian body 112 and prevent migration of the ultrasound imaging marker 110 therein. The at least one positioning end cap 152 is preferably constructed of polypropylene or similar material and functions to prevent migration of the ultrasound imaging marker 110.

As shown in FIG. 15, the outer shell may includes a pair of positioning end caps 152 that are each attached to an end of the ultrasound imaging marker 110 using a frictional fit and preferably an adhesive. Each of the pair of positioning end caps 152 is preferably shaped and constructed to prevent migration of the ultrasound imaging marker 110 within the mammalian body 112.

As shown in FIG. 16, the ultrasound imaging marker 110 may be positioned within a central body 154 having a slot 156 shaped to receive the ultrasound imaging marker 110. The central body 154 is integral with the at least one positioning end cap 152 and also constructed of a biocompatible material, preferably also polypropylene, polyethylene, or similar material. The at least one positioning end cap 152 includes at least one concentric furrow 158 that helps stabilize the ultrasound imaging marker 110 within the mammalian body 112.

Figure 17:
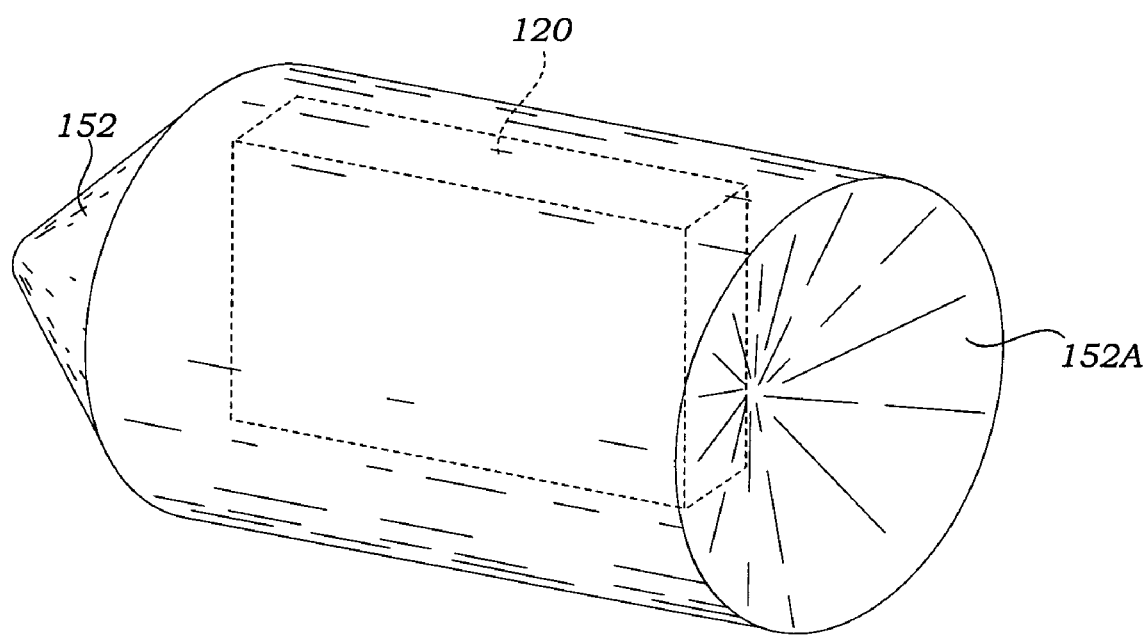
FIG. 17 is a perspective view of the ultrasound imaging marker including another embodiment of the pair of positioning end caps.

As shown in FIG. 17, the ultrasound imaging marker 110 may be molded within the central body 154. In this embodiment, the central body 154 includes one end cap 152 that protrudes outward, and an indented end cap 152A. The indented end cap 52A serves the same purpose as the other end cap 152, but the indented shape allows the ultrasound imaging markers 110 to be packed more tightly end to end.

While some embodiments have been described, those skilled in the art can devise alternative means for preventing migration 150 of the ultrasound imaging marker 110 within the mammalian body 112. Alternative examples include, but are not limited to, attaching the ultrasound imaging marker 110 to a fixed body such as a prosthesis, staple, or other body, or to a fixed portion of the mammalian body 112, such as a bone. The ultrasound imaging marker 110 can also be built directly into a prosthesis, screw, or other implant before the implant is placed in the mammalian body 112. The ultrasound imaging marker 110 can also be sewn or stapled into position. The ultrasound imaging marker 110 can also be associated with a surgical instrument such as the ultrasound transducer 24, the stent insertion device 32, and the ablation device 48 described herein, so that the surgical instrument can be viewed using the ultrasound device 113. Those skilled in the art can devise alternative mechanisms or techniques for fastening the ultrasound imaging marker 110 into its position adjacent to the location 111 being marked.

As shown in FIGS. 18–19, the surgical marking system preferably includes the insertion device 160 for inserting the ultrasound imaging marker 110 adjacent the location 111 in the mammalian body 112. The insertion device 160 may include an insertion device body 162 and a hand grip 164 that extends downwardly from the insertion device body 162. A trigger 166 extends downwardly from the insertion device body 162 in front of the hand grip 164 and is pivotally attached to the hand grip 164 with a pivot pin 168 for operative movement, as described below. The term "trigger" 166 is not limited to the embodiment shown, but should be construed to include equivalent mechanisms such as any manner of buttons, slides, electromechanical mechanisms, and other means of triggering the insertion device 160 that can be devised by those skilled in the art, whether directly or remotely actuated.

As shown in FIGS. 20–21, the insertion device 160 preferably has a cannula 170 with an insertion tip 172 for inserting the ultrasound imaging marker 110. The insertion tip 172 has an interior cannula chamber 174 shaped to receive the ultrasound imaging marker 110 and dispense the ultrasound imaging marker 110 through a cannula opening 176 of the insertion tip 172 into the mammalian body 12. In the preferred embodiment, as shown in FIG. 10, the interior cannula chamber 174 is shaped to receive three of the ultrasound imaging markers 110; however, the interior cannula chamber 174 can be adapted to hold any number of the ultrasound imaging markers 110, depending upon the needs of the users.

The insertion device 160 further includes a means for ejecting 178 one of the ultrasound imaging markers 110 upon actuation of the trigger 166. In one embodiment, as shown in FIG. 19, the means for ejecting 178 includes an elongate shaft 180 attached to a plunger 182 that is operably positioned within the cannula 170. When the trigger 166 is squeezed towards the hand grip 164, the trigger 166 pivots about the pivot pin 168 so that an upper portion 188 of the trigger 166 contacts one of a plurality of engagement ridges 190 of the elongate shaft 180. The plurality of engagement ridges 190 are spaced approximately the length of the ultrasound imaging markers 110 so that advancing the shaft the length of one of the plurality of engagement ridges 190 ejects one of the ultrasound imaging devices. The trigger 166 is designed to remain in contact with the engagement ridge 190, and thereby advance the shaft, until the plunger 182 has moved far enough to eject the one of the ultrasound imaging markers 110. The shaft further includes friction ring 192, preferably constructed of rubber or similar material, which frictionally contacts the insertion device body 162 and prevents the shaft from retracting when the trigger 166 pivots back to the original position. Once the trigger 166 has returned to the original position, the upper portion 188 contacts the next of the plurality of engagement ridges 190, ready to advance the plunger 182 again and eject another of the ultrasound imaging markers 110. While the mechanism described is one possible preferred, alternative structures can also be used. In one alternative embodiment, in which the insertion device 160 holds only one ultrasound imaging marker 110, a simple plunger mechanism can be used without the need for the more complex mechanism described.

Also, while the embodiment described includes a cannula 170 that is rigid and that includes a rigid connection, the plunger 182 and elongate shaft 180, it is also possible to utilize a flexible actuation mechanism (not shown) that enables the surgeon to direct the insertion tip 172 along a convoluted route to the location 111. Such an embodiment is useful for endoscopic delivery. Certain surgical procedures, such as arthroscopic surgery, often require complex delivery systems that often do not provide a direct route to the location 111.

As shown in FIG. 21, the invention further includes a method for marking a location 111 in a mammalian body 112 using the above-described surgical marking system. The ultrasound imaging marker 110 is provided operably positioned within the insertion device 160 and the cannula 170 of the insertion device 160 is inserted into the mammalian body 112 until the insertion tip 172 is adjacent the location 111. Finally, the ultrasound imaging marker 10 is ejected, as described above, so that it remains adjacent the location 111.

As shown in FIGS. 22–23, the surgeon can use the ultrasound device 113 to check the location 111 of the ultrasound imaging marker 110. The transducer 114 is operably connected to the ultrasound device 113 and placed over the location 111 and the ultrasound waves 115 are directed at the ultrasound imaging marker 110, which is plainly visible to the ultrasound device 113, as described above. This enables the surgeon to periodically check the location 111 of the ultrasound imaging marker 110 to see if the ultrasound imaging marker 110 has moved, or as a locator to direct future surgical procedures.

In one example, the ultrasound imaging marker 110 can be used during surgery to remove a tumor 111 from a breast. In this example, shown in FIG. 21, when a biopsy is removed from the tumor 111, the ultrasound imaging marker 110 may be positioned adjacent the edge of the tumor 111, or a plurality of the ultrasound imaging markers 110 can be placed around the perimeter of the tumor 111. Once the biopsy has been analyzed and found to be cancerous, the effectiveness of the chemotherapy and/or radiation therapy can be assessed by checking the positions of the plurality of ultrasound imaging markers 110 using ultrasound or radiography to see if the tumor 111 is growing or shrinking. If the surgeon decides to remove the tumor 111 surgically, the perimeter of the tumor 111 can be readily ascertained with reference to the plurality of ultrasound imaging markers 110. Finally, one the tumor 111 has been removed, another ultrasound imaging marker 110 can be left to mark the place from where the tumor 111 was removed. In the future, if further surgery is required, or any follow-up biopsies are required, the ultrasound imaging marker 110 can be used to readily direct the surgeon back to the prior location of the tumor 111.

While the invention has been described with reference to at least one preferred embodiment, it is to be clearly understood by those skilled in the art that the invention is not limited thereto. Rather, the scope of the invention is to be interpreted only in conjunction with the appended claims. All patents, patent applications, and other documents and printed matter cited or referred to in this application is hereby incorporated by reference in full.

What is claimed is:

1. An ultrasound imaging system, comprising:
an ultrasound probe adapted to be placed in an instrument working channel of an endoscope, the ultrasound probe having a probe housing; an ultrasound transducer mounted within the probe housing; and an elongate flexible cord extending from the probe housing, the elongate flexible cord being adapted to fit through the instrument working channel of the endoscope and operably connect the ultrasound transducer with a computer; and
a biomarker mounted on the ultrasound probe,
wherein the biomarker includes a MEMS housing constructed of a biocompatible material.

2. The ultrasound imaging system of claim 1 wherein the biomarker includes a wave-guide feature that is integral with the MEMS housing and adapted to resonate when struck by an excitation signal.

3. The ultrasound imaging system of claim 1 wherein the wave-guide feature includes a plurality of wave-guide rods that are integral with and extend from a dielectric base.

4. The ultrasound imaging system of claim 3 the plurality of wave-guide rods are disposed on a plane and in parallel orientation.

* * * * *